(12) United States Patent
Jorgensen et al.

(10) Patent No.: US 6,720,984 B1
(45) Date of Patent: Apr. 13, 2004

(54) CHARACTERIZATION OF BIOELECTRIC POTENTIALS

(75) Inventors: Charles C. Jorgensen, Palo Alto, CA (US); Kevin R. Wheeler, Mountain View, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 362 days.

(21) Appl. No.: 09/606,107

(22) Filed: Jun. 13, 2000

(51) Int. Cl.⁷ .................................................. G09G 5/00
(52) U.S. Cl. ...................................... 345/863; 600/300
(58) Field of Search ................................. 345/700–702, 345/863, 156, 161, 179; 382/119, 181, 186–189, 209; 600/300, 546; 707/541; 715/541

(56) References Cited

U.S. PATENT DOCUMENTS

| | | | |
|---|---|---|---|
| 5,482,051 A | * 1/1996 | Reddy et al. ................ | 600/546 |
| 5,559,897 A | * 9/1996 | Brown et al. ................ | 382/186 |
| 5,875,257 A | 2/1999 | Marrin et al. ................ | 382/107 |
| 5,901,246 A | 5/1999 | Hoffberg et al. ............ | 382/209 |
| 5,920,477 A | 7/1999 | Hoffberg et al. ............ | 382/181 |
| 6,001,065 A | 12/1999 | DeVito ........................ | 600/544 |
| 6,061,652 A | 5/2000 | Tsuboka et al. ............ | 704/245 |
| 6,244,873 B1 | * 6/2001 | Hill et al. .................... | 434/236 |
| 6,304,674 B1 | * 10/2001 | Cass et al. ................... | 382/224 |
| 6,440,067 B1 | * 8/2002 | DeLuca et al. ............. | 600/300 |

OTHER PUBLICATIONS

Jorgensen et al, "Bioelectric Control of a 757 Class High Fidelity Aircraft Simulation", Computational Science Division, Papers and Publications Archive, online Aug. 9, 1999, <URL: http://ic.arc.nasa.gov/publications/pdf/1999–0108.pdf>, pp. 1–8.*

Putnam et al, "Real–Time Computer Control Using Pattern Recognition of the Electromyogram", Biomechanics, Rehabilitation, Electrical Phenomena, Biomaterials, IEEE, vol. 3, conf. 15, Oct. 28, 1993, pp. 1236–1237.*

(List continued on next page.)

*Primary Examiner*—Sy D. Luu
(74) *Attorney, Agent, or Firm*—Robert M. Padilla; John F Schipper; Carla M. Wong

(57) ABSTRACT

Method and system for recognizing and characterizing bioelectric potential or electromyographic (EMG) signals associated with at least one of a coarse gesture and a fine gesture that is performed by a person, and use of the bioelectric potentials to enter data and/or commands into an electrical and/or mechanical instrument. As a gesture is performed, bioelectric signals that accompany the gesture are subjected to statistical averaging, within selected time intervals. Hidden Markov model analysis is applied to identify hidden, gesture-related states that are present. A metric is used to compare signals produced by a volitional gesture (not yet identified) with corresponding signals associated with each of a set of reference gestures, and the reference gesture that is "closest" to the volitional gesture is identified. Signals representing the volitional gesture are analyzed and compared with a database of reference gestures to determine if the volitional gesture is likely to be one of the reference gestures. Electronic and/or mechanical commands needed to carry out the gesture may be implemented at an interface to control an instrument. Applications include control of an aircraft, entry of data from a keyboard or other data entry device, and entry of data and commands in extreme environments that interfere with accurate entry.

22 Claims, 9 Drawing Sheets

OTHER PUBLICATIONS

"Computer Input Device Via Nerve Signal Detection", IBM Technical Disclosure Bulletin, vol. 32, No. 3A, Aug. 1, 1989, pp. 424–426.*

J. MacQueen, "Some Methods for Classif and Analysis of Multivariate Distribs", Fifth Berkeley Symp. on Math. Stat, 1967, vol. 1, pp. 281–297.

B. Sklar, *Digital Communications*, PTR Prentice Hall, New Jersey, 1988, pp. 333–338.

H.S. Lusted and R.B. Knapp, "Controlling Computers with Neural Signals", Scientific American, Oct. 1996, pp. 82–87.

A. Viterbi, "Error Bounds for Convolutional Codes", IEEE Trans. Info. Theory, vol. IT–13, 1967, pp. 260–269.

L.R. Rabiner and B.H., Juang, "An Introduction to Hidden Markov Models", IEEE ASSP Magazine, vol. 3, 1986, pp. 4–16.

L.R. Rabiner, "A Tutorial on Hidden Markov Models and Selected Appls in Speech Recognition", Proc. IEEE, vol. 77, 1989, pp. 257–286.

* cited by examiner

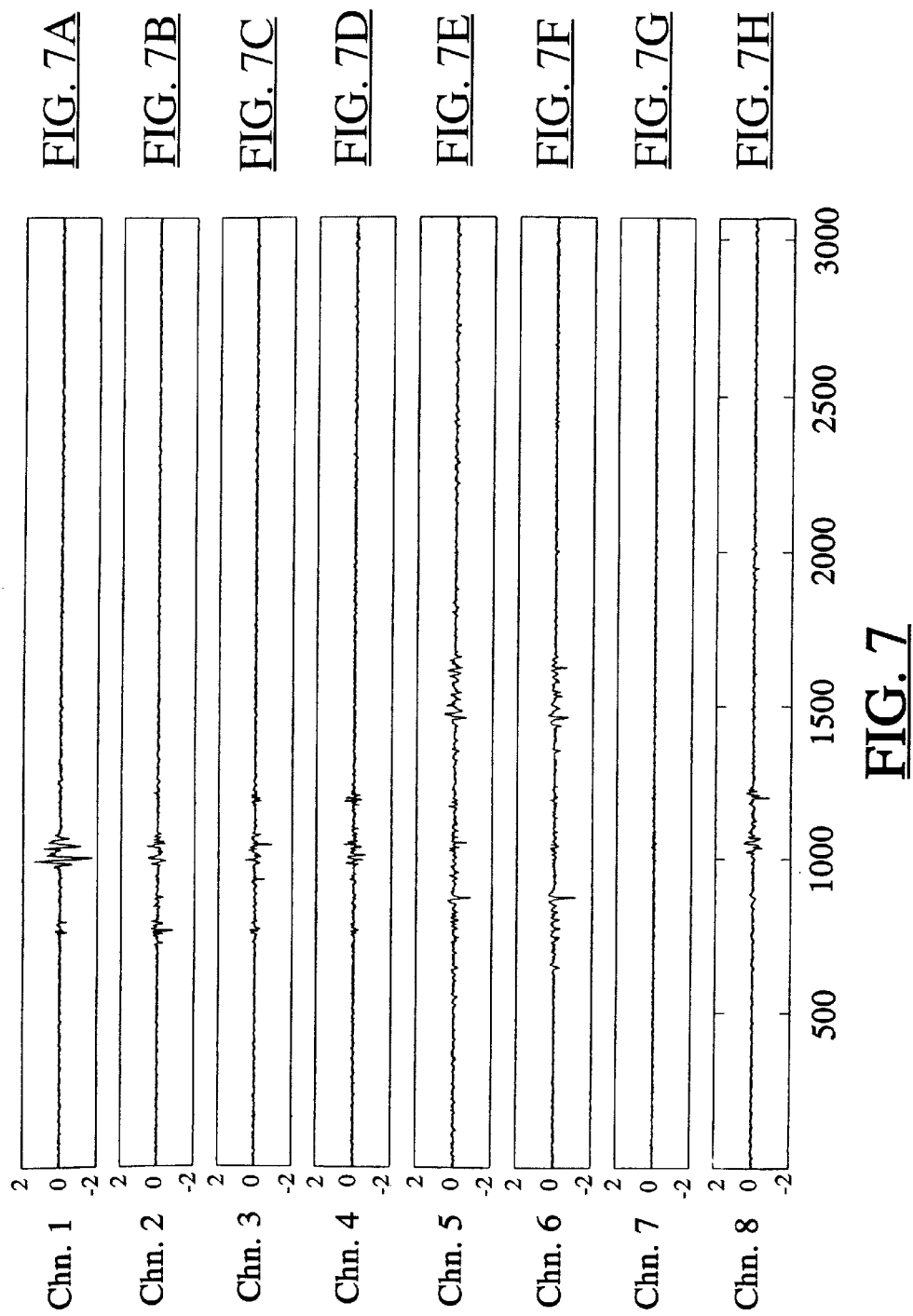

CHARACTERIZATION OF BIOELECTRIC POTENTIALS

FIELD OF THE INVENTION

This invention relates to monitoring and characterization of bioelectric. potentials in muscles and related body components that arise from gestures.

BACKGROUND OF THE INVENTION

Standard interface and signal input devices, such as a keyboard, mouse, light pen and/or touch screen, are now well known and well used, especially in environments that rely upon computer signal processing. However, in an environment where the operator's body is moving, where the operator's attention is divided while certain tasks are being performed, where extremes of high or low temperature, dim light, noise or similar interfering features are present, a standard interface may be unreliable. For certain classes of signal inputs by a (human) operator, monitoring and characterization of bioelectric potentials generated in the body by operator gestures are likely to be more reliable, if it is possible to classify and distinguish between different groups of bioelectric signals associated with different gestures.

The minimum size of a computer or other signal processor is rapidly decreasing, and the sizes of many of these processors today are already smaller than the sizes of the conventional data/command entry interfaces, such as keyboards, chording keyboards, touch screen locations and light pens, that are available for data/command entry. Development of a system that monitors and analyzes bioelectric potentials generated in the body by gestures would allow these conventional interfaces to be replaced by virtual data/command entry interfaces that are not limited by the minimum size of the interface. With such a virtual system, the operator makes a gesture that would be carried out on an interface of conventional size, if such an interface were present, and the system monitors and interprets the bioelectric potentials generated in a selected part of the operator's body and translates these bioelectric potentials to one or more electronic commands for a selected instrument (computer, signal processor, vehicle controller, cellphone, etc.)

Classification of, and distinguishment between, different groups of bioelectric signals is especially difficult, for the following reasons: (1) the bioelectric signals for most gestures, except those involving movement of major muscle groups, usually have very low amplitudes, of the order of 0.01 –10 $\mu$volts; (2) a bioelectric signal amplitude is often accompanied by a dc voltage offset, which compromises the dynamic range over which a voltage sensor can operate; (3) the bioelectric signals of interest are often accompanied by other body signals that mask or interfere with recognition of the signals of interest; (4) many of the bioelectric signals of interest lie in the frequency range 30–300 Hz, and the environment is bathed in extraneous signals in the range 50–60 Hz, arising from the drive current supplied to drive most electrical instruments; (5) the bioelectric signals of interest are transported along nerve cords within the body, and the signals sensed at the surface of a body's skin are thus filtered by the various cutaneous and subcutaneous layers a nerve cord signal must pass through to reach the surface; it is estimated that the electrical signals are attenuated by a factor of about 30 in passing through a person's skin; and (6) physical differences, such as different hand sizes or arm lengths, different angles of application, different muscle sizes, and different amounts of layered fat adjacent to a muscle group.

What is needed is an approach that permits non-invasive, non-intrusive monitoring and analysis on a person's body of bioelectric signals generated by each of a selected group of gestures and identification of one or more particular states that are characteristic of a particular gesture. Preferably, the analysis should be rapid and provide real time, on-line identification of a gesture that is being presently, executed by the person. Preferably, the monitoring and control should be performed by a small appliance, worn on the body, that either performs part or all of the analysis or transmits the data sensed by the appliance to a nearby processor that provides the analysis nearly instantaneously.

SUMMARY OF THE INVENTION

These needs are met by the invention, which provides a system, and a method for using the system, that senses bioelectric signals generated within a person's body in response to performance of a gesture by the person, using two or more spaced apart electrodes located on the body. The system forms and analyzes differences of signals generated at the sensing locations in each of a sequence of preferably-overlapping time intervals, using hidden Markov modeling, neural net analysis or another suitable technique to identify a sequence of states that is associated with and/or characteristic of the bioelectric signals that accompany the gesture. An initially chosen set of coarse and fine gestures includes the following gestures using a hand and/or arm: making a stop motion; making a fist; making a come motion; making a thumb up motion; making a thumb down motion; tapping with at least one finger; reaching for and depressing at least one key on a keyboard; moving a joystick in at least one of the directions forward, backward, right and left; touching a joystick without movement of the joystick; grasping and positioning a stylus near a touch screen; and similar gestures in a three-dimensional virtual environment. The gestures to which the invention applies are not limited to this initial set, but the invention can be demonstrated using this set. The signals monitored in the invention are primarily electromyographic (EMG) signals that arise from motion of one or more muscles. Other classes of signals include electroencephalographic (EEG) and electrooculographic (EOG) signals, which are associated with signals originating in the brain and in the eye, respectively.

BRIEF DESCRIPTION OF THE DRAWINGS

FIGS. 7A–7H illustrate raw EMG signals sensed for a test subject whose gesture is typing an alphanumeric character on a keyboard.

DESCRIPTION OF BEST MODES OF THE INVENTION

Figures 1, 2:
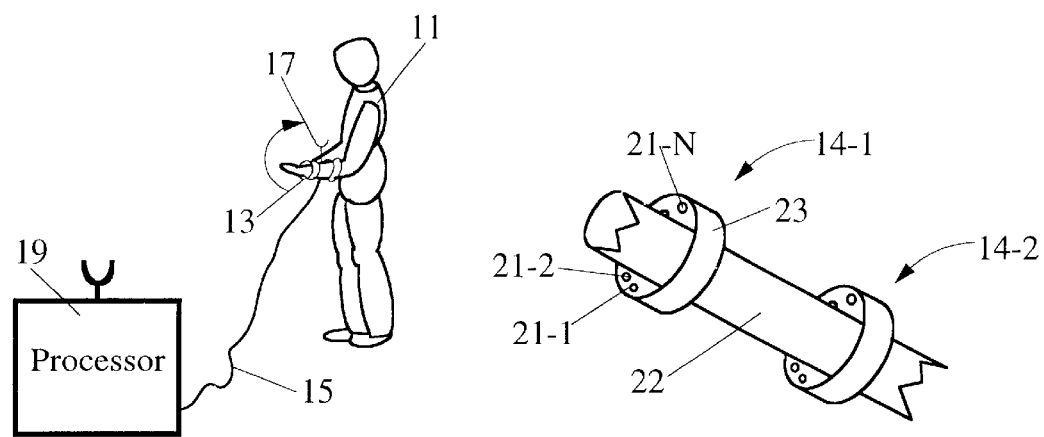
FIG. 1 illustrates an environment in which the invention may be practiced
FIG. 2 illustrates a suitable arrangement of electrodes as part of a sensor.

FIG. 1 illustrates use of the invention in one environment. Herein, a "person" will refer to a human being and to other animals. A test subject or person 11 wears a small appliance 13 on a limb, such as a forearm, a hand, a finger, a leg, a foot, a toe or another part of the person's body, in order to sense, and to ultimately analyze, one or more bioelectric signals associated with one or more selected gestures performed by the person. A typical gesture will last between 0.3 and 3 sec. Analysis of the bioelectric signals can be performed, in part or in whole, by the appliance 13, and the resulting data signals can be transmitted, using an attached cable 15 or using a suitable rf, microwave or infrared transmitter 17, to a signal processor 19, including a computer, that is programmed to respond to receipt of such signals. Alternatively, the appliance 13 may transmit raw signal data, using the cable 15 or the transmitter 17, to the processor 19 for analysis of and response to the sensed signals. The appliance 13 includes two or more spaced apart sensors 14-1, 14-2, . . . , illustrated in FIG. 2, each including one or more electrodes that sense bioelectric signals appearing at the surface of the skin of the monitored person 11.

The sensors 14-1, 14-2, . . . shown in FIG. 2 may each include one or more spaced apart, wet or dry electrodes 15 that are arranged in a selected pattern on the monitored body part 12. For example, a group of electrodes 21-1, 21-2, . . . , 21-N may be provided as part of a bracelet 23 that encircles a limb 22, such as a finger, a hand, a wrist, a forearm, an arm, a thigh, a leg, an ankle a foot, a toe, with each electrode sensing more or less independently the bioelectric (EMG) signals that appear at the region of body surface covered by that electrode.

EMG signals originate during muscle contraction and/or relaxation. A skeletal muscle includes muscle fibers that are activated or enervated by moto-neurons linked to the spinal cord or brainstem of the body. One moto-neuron may control as few as 1–10 fibers (an example is an eye muscle) or may control as many as 1000 fibers in a major muscle group. Fibers that are associated with the same moto-neuron are often sparsely located within that muscle. A fiber may be associated with, and partly controlled by, more than one moto-neuron.

Figure 3:
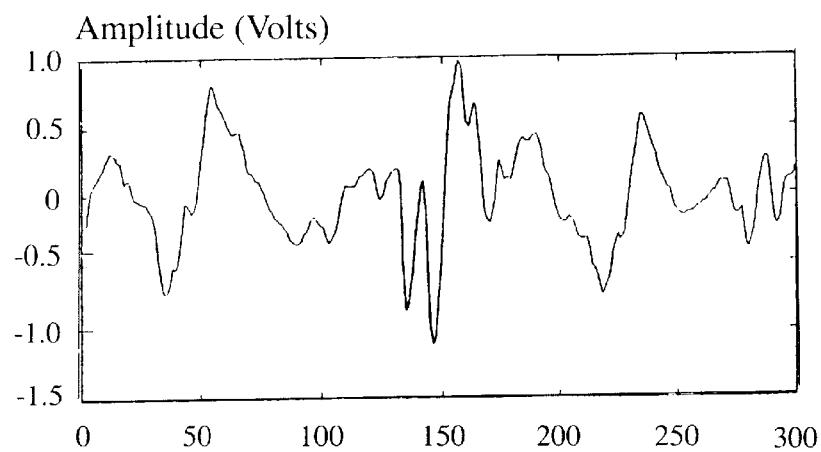
FIGS. 3 and 4 graphically illustrate EMG signal amplitudes from contraction of a large muscle and EMG signal spectrum from repeated thumb movements, respectively.

During muscle contraction, a depolarization wave of negative ions, which manifest muscle action potential, moves along the muscle fibers from enervation zones (motor connection points) to tendons that will respond to receipt of this wave. Although this fluctuation in electrical potential is partly dissipated by the skin tissue and overlying muscles, a portion of this fluctuation reaches the skin surface and can be recorded, after suitable amplification. Surface EMG signals can be measured non-invasively by attaching a silver/silver chloride dry electrode, or a silver/silver chloride wet electrode, to the person's body. A contraction of a single motor unit typically lasts 5–10 milliseconds, after which the fibers relax. FIG. 3 graphically illustrates amplitudes from a typical EMG signal arising from a biceps contraction, sampled at a rate of 2000 sec$^{-1}$. A recorded EMG signal at a location on the skin rarely includes activity from only one, isolated motor unit, because collaborative action by several motor units is often required to perform a body movement, even a small hand or finger gesture.

A surface EMG signal is thus an aggregate of asynchronous, transient discharges of many motor units. The combined effect of these asynchronous discharges is perceived as a smooth action rather than a jerky action. Depending upon the required strength of contraction and muscle condition (e.g., fatigue), the firing rate of a single motor unit can be as high as 70 Hz, with a firing rate of 20–40 Hz being typical. An EMG signal amplitude depends upon muscle force, size of the motor units that respond, distance of a motor unit from an electrode, required contraction level and muscle condition, among other things.

Figure 4:
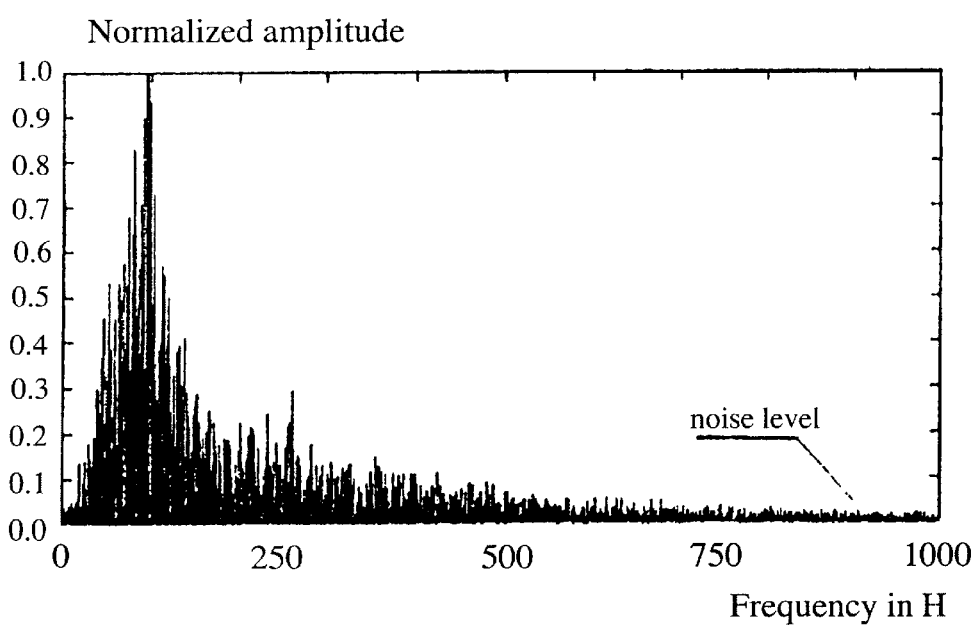

Intensive physical effort can produce a momentary increase in amplitude of EMG signals, to 0.01 volts or higher, in the skin area covering a large limb muscle. Usually, however, the EMG signal amplitudes are much lower, with typical amplitudes in the range 0.1–1 mvolt. A useful spectrum of surface EMG signals typically runs from 10 Hz to 1 kHz, although some workers recommend use of a higher upper bound, such as 2 kHz. FIG. 4 is a typical surface EMG signal spectrum, averaged over several adjacent electrodes and over time, for repeated movements of a thumb (small muscle). The main EMG activity appears in low frequencies, in a range 30–150 Hz. Because of the strong filtering and attenuation effects of the skin, the spectrum is flat above 1 kHz, except for spurious noise. Recording of surface EMG signals with frequencies below 10 Hz is also preferably avoided, because this range is often corrupted by the presence of body movement artifacts, including the effect of moving cables, if cables are used to transmit the recorded data from the body. An EMG spectrum, such as that shown in FIG. 4, often has a strong contribution from the 50–60 Hz signals due to drive currents used to power household and commercial electrical devices. These 50–60 Hz extraneous signals cannot be removed from an EMG spectrum, for example, by using a notch filter, without removing a substantial part of the desired information in this part of the spectrum. However, use of difference signals eliminates much of this interference.

Miniature pre-amplifiers, with signal amplification ratios preferably in a range of 1000–2000, bandpass signal filters, and common mode rejection ratios of at least 100–130 dB, are preferably incorporated in the sensors placed on or adjacent to the body. EMG signal dc offset and "contributions from frequencies below 10 Hz are preferably removed with a first order or higher order filter, implemented as an integrator. EMG signal contributions above 1 kHz are preferably removed with a high order filter, such as a fourth 1order Bessel anti-aliasing filter. The EMG signals are preferably over-sampled at a 6 kHz sampling rate, then digitally filtered and down-sampled to a 2 kHz rate. In one version, a ring or bracelet having eight electrodes is attached to a body part to be monitored, and the sensed EMG signals are transmitted to and analyzed by a computer using double shielded composite cable.

Tests on persons with electrodes displaced from selected reference locations by varying distances (1–3 mm up to 1–2 cm) indicate that these displacements have unpredictable effects on the EMG signals recorded at each electrode. Thus, an effort should be made to ensure that the electrode locations are as close as possible to the reference locations for each test subject. Subject-to-subject variations in EMG signals for a single gesture are substantial but can be compensated by using the system to "learn" the characteristic responses for a given subject for each gesture of interest, much as a voice recognition system must "learn" the speech patterns of a given test subject. External influences, such as consumption of caffeine, biorhythm patterns and performance fatigue also have noticeable effects on EMG signals recorded for a test subject.

Figure 5:
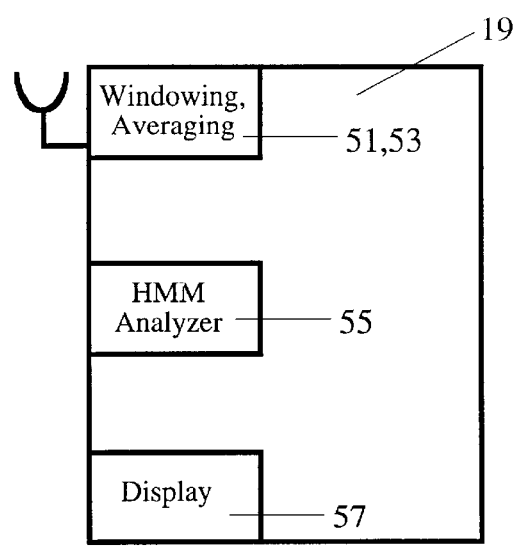
FIG. 5 is a schematic view of apparatus suitable for processing EMG signals.

In one embodiment, the pre-amplified and filtered EMG signals sf(t;d;m) from a selected gesture, for each test (index d) and each of M channels (m=1 ..., M; M≧2), are received by a signal processor 19, shown in FIG. 5. A moving average, using magnitudes |sf(t;d;m)| of signals, is formed in a time windowing and time averaging module 51. The time averaging module 51 then provides moving average values that are analyzed and used to divide a time interval into a sequence of time partition intervals ("time slices"), tpi≦t≦tpi'. An average magnitude OTA(i;d;m) of each filtered signal sf(t;d;m) for each channel (m) within time partition interval (i) is determined by a statistical averaging module 53, and an M-dimensional vector fv(i;q(i)) is formed from further processing of the average values OTA. The vectors fv are analyzed using a hidden Markov model ("HMM") analyzer 55 to identify and distinguish hidden states that are associated with the selected gesture. Alternatively, a hybrid HMM analysis and/or neural net analysis is used by the module 55 to identify and distinguish hidden states that are associated with the selected gesture. Optionally, results of the signal processing are shown alphanumerically or graphically on a display screen 57.

Figure 6A:
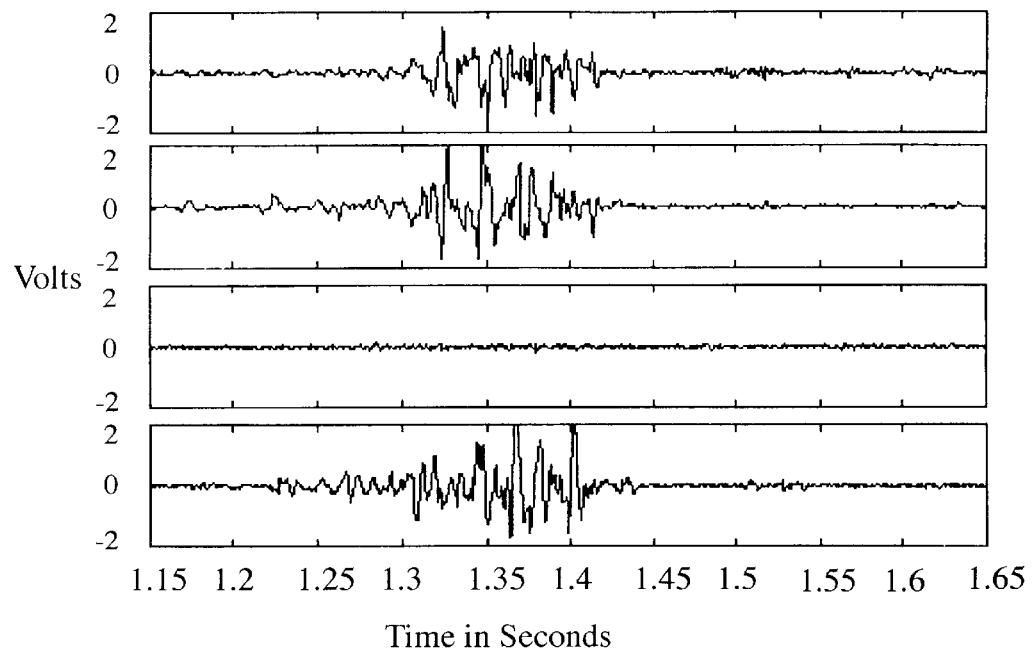
FIGS. 6A, 6B and 6C are graphical views of raw and processed EMG signal data collected in a representative task (joystick manipulation).
Figure 6C:
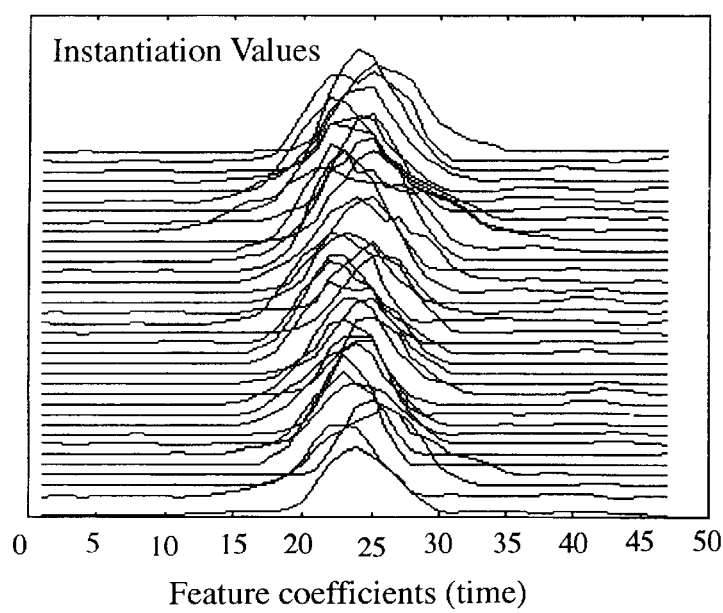
Figure 6B:
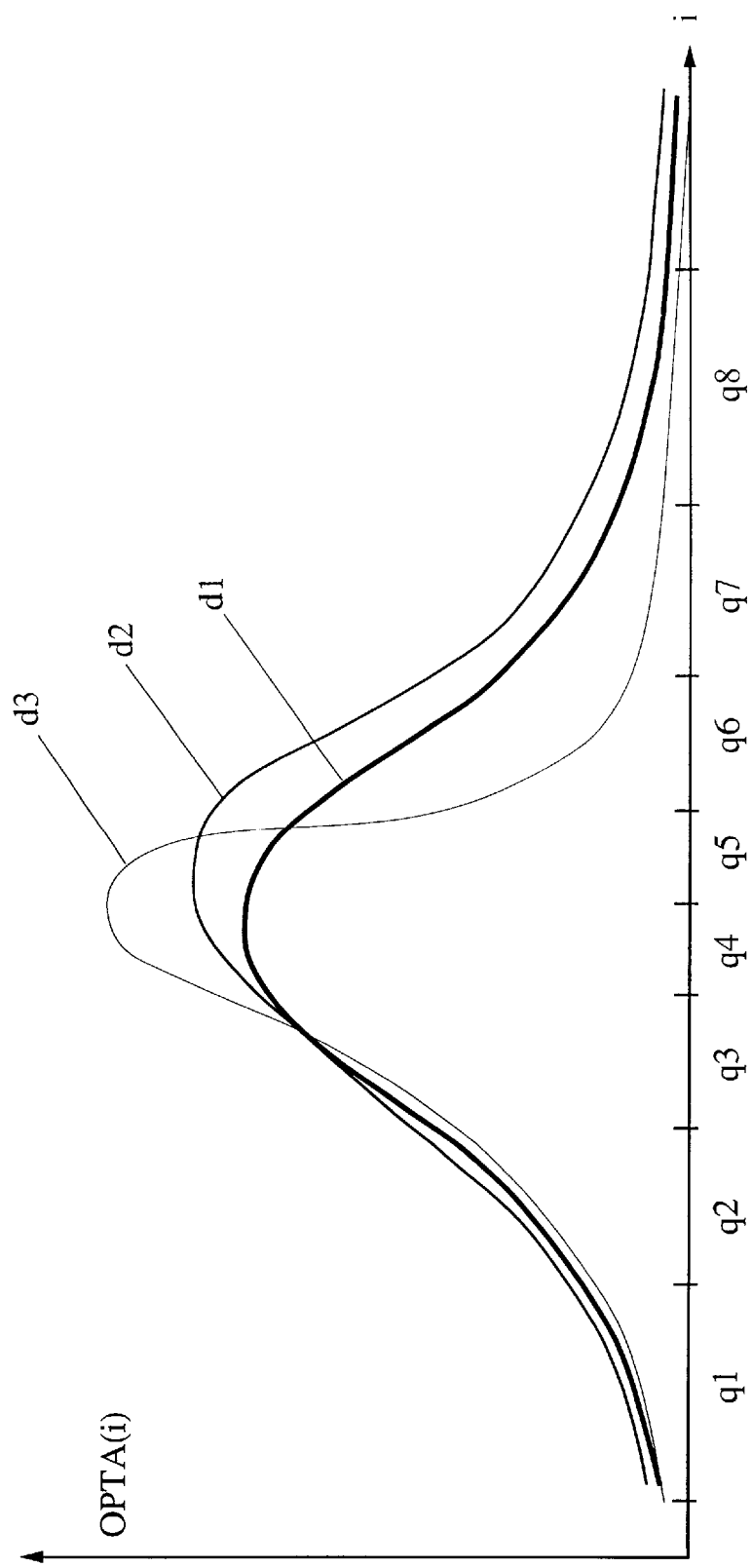

The magnitude of each of a group of raw or filtered EMG signals, shown graphically in FIG. 6A for a representative task, such as joystick manipulation, is integrated over a selected time segment (i) and produces overlapping average values OTA(i;d;m) such as those shown in FIG. 6B. Each of the curves, labeled d1, d2 and d3, in FIG. 6B, corresponds to a separate test of a single gesture. In one example, each time segment includes 128 consecutive samples, taken at 2000 samples/sec, and two consecutive time segments, i and i+1, overlap by either 96 or 112 samples (overlap factor of 75 percent or 87.5 percent). Where a sequence of such tests for a single gesture is conducted, a sequence of moving time average curves OTA(i;d;m), indexed by d, is obtained, as illustrated in FIG. 6C. The collection of curves OTA(i;d;m) is analyzed to select a sequence of Q segments, $I_{q-1}+1 \leq i \leq I_q$ (q=1, 2, ..., Q) according to a selected criterion. These Q segments, and the distributions OTA(i;d;m) associated with each segment, are used to define Q states that are subjected to hidden Markov modeling (HMM).

In Markov modeling, an assumption is made that an ordered time series can be modeled as a chain or sequence of events, using a memoryless channel or stationary process, in which a probability of transition from a present state to a subsequent state depends only upon the present state and the subsequent state. The series is modeled using a random variable that can be in one of several (intermediate) states. These states may be hidden states, used for mathematical purposes but not inherent in the physical process represented by the sequence of events. As the series progresses through the sequence of events, the probability of observing a particular sequence of events is calculated. Rabiner, in Proc. I.E.E.E. vol. 77 (1989) pp. 257–285, provides a tutorial discussion of hidden Markov modeling, with applications to speech recognition.

An HMM approach implicitly assumes that the time series is stationary, although EMG signals are inherently non-stationary. This discrepancy has some effect on the accuracy arising from use of an HMM but allows quantitative modeling for predictive purposes. The process to which the HMM is applied is assumed to be a left-to-right process, in which the system always begins in a definite initial state, proceeds through intermediate states to a definite final state, and does not return to any intermediate state. The initial HMM state is determined using a K-means clustering algorithm. Training of the HMM states uses the Baum-Welch training algorithm, described by L. R. Rabiner and B. H. Juang, "An Introduction to Hidden Markov Models", I.E.E.E. ASSP Magazine, vol. 3, 1986, pp. 4–16. The information contained in this article is incorporated herein. A state sequence representing a candidate gesture is subjected to a Viterbi-type analysis of state vector transitions, as described in A. Viterbi, "Error Bounds for Convolutional Codes and an Asymptotically Optimum Decoding Algorithm", I.E.E.E. Trans. on Info. Theory, vol. IT-13, 1967, pp. 260–269 and in B. Sklar, *Digital Communications*, PTR Prentice Hall, Upper Saddle River, N.J., 1988, pp. 333–338. Repetition reduces the possibility of acceptance of spurious signals as representing a gesture.

Assume that a sensor for each of M channels receives a time varying signal s(t;d;m) (m=1, ..., M) corresponding to a selected gesture and a single test, referenced by the index d. FIGS. 7A–7H graphically illustrate a set of raw EMG data signals, sampled at 6000 per second, filtered and down-sampled to 2000 per second, for a test subject whose gesture is typing a single alphanumeric character, such as the numeral "1", on a keyboard, for M=8 channels. After filtering and downsampling, the resulting filtered signal sf(t;d;m) will vary from test to test (d) for a single gesture and for a fixed test subject.

Figure 8A:
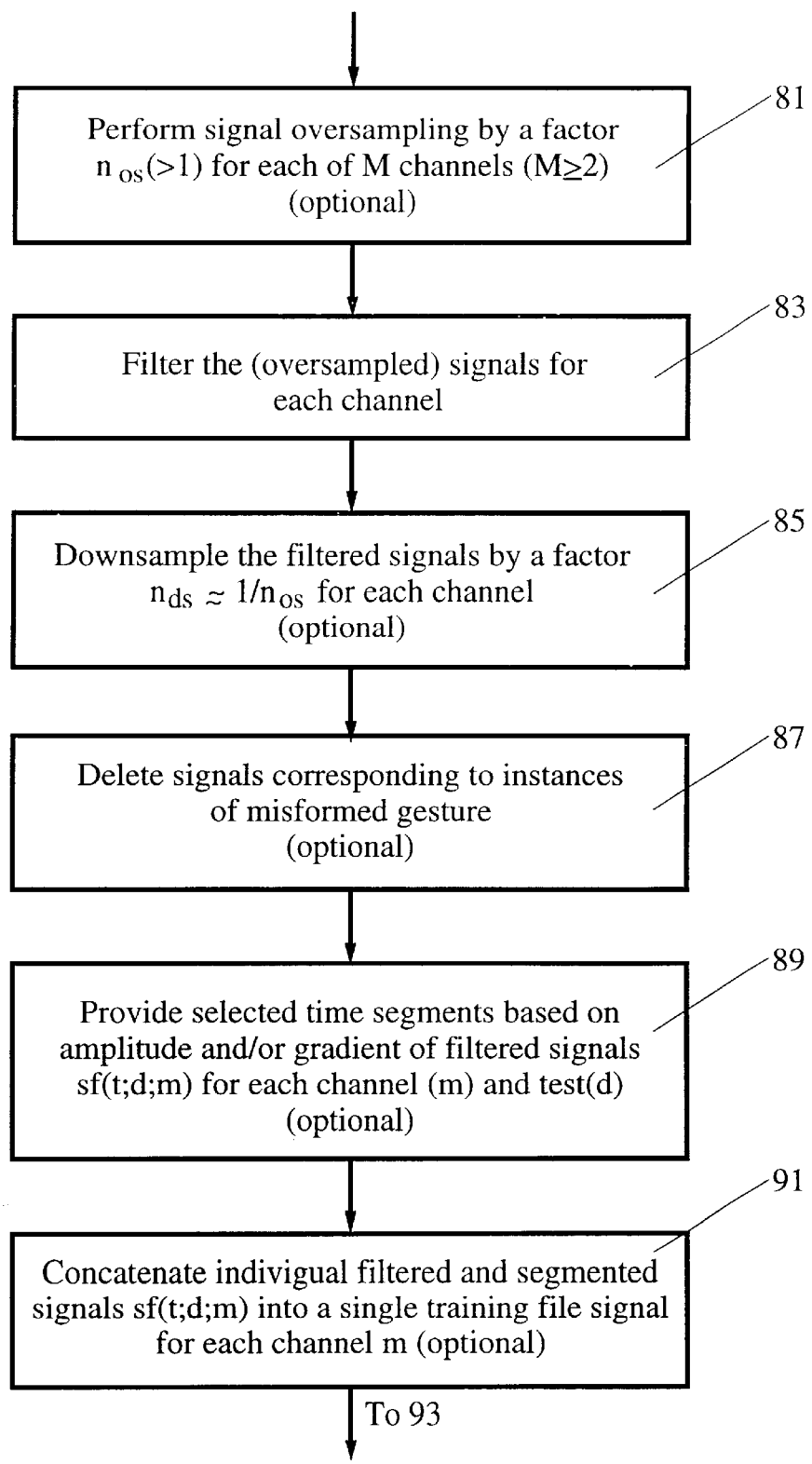
FIGS. 8A/8B and 9A/9B are flow charts for practicing the invention using hidden Markov modeling or other suitable analysis.
Figure 8B:
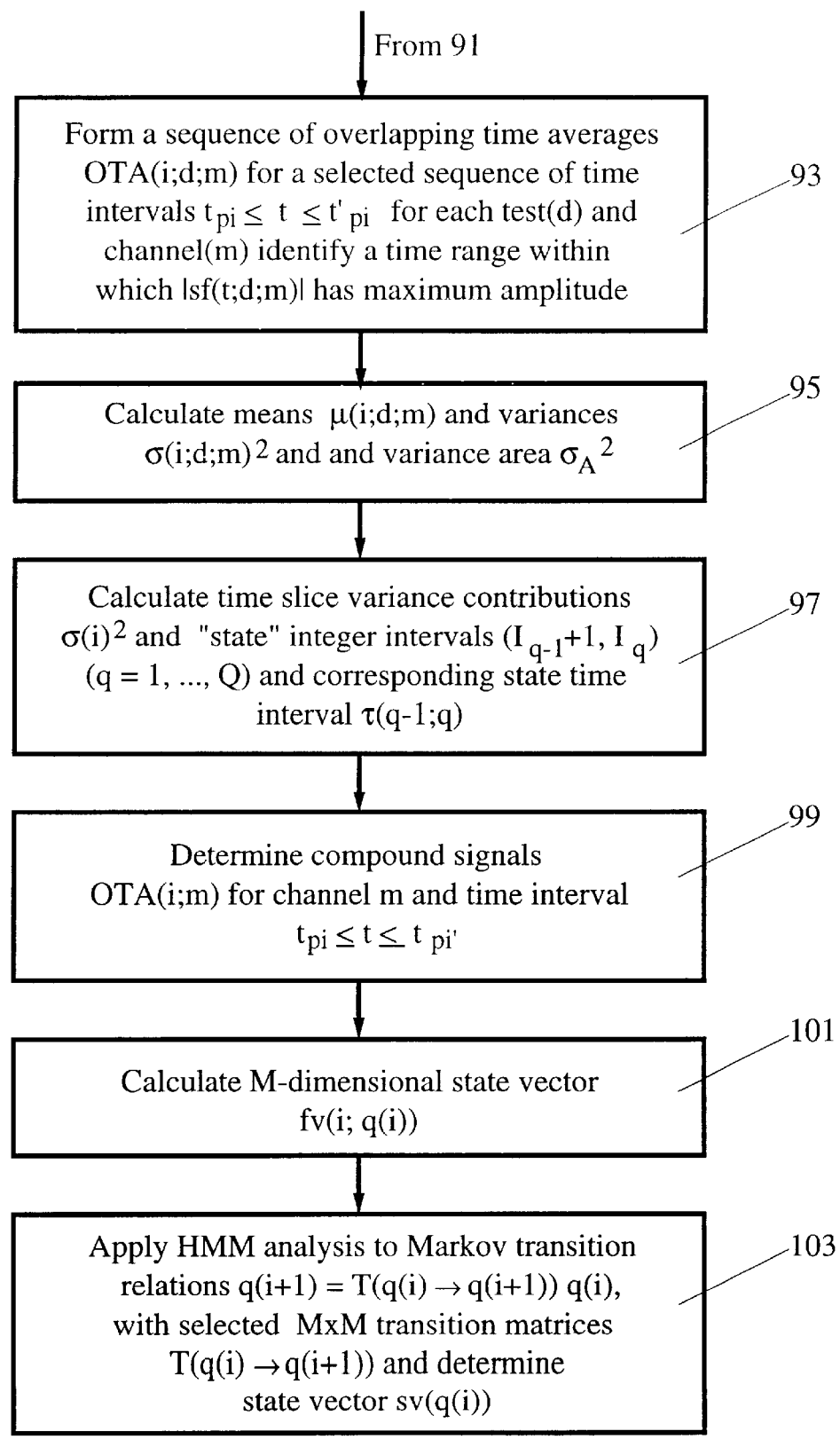

FIG. 8 is a flow chart illustrating the processes performed in applying pattern recognition to EMG data. In step 81, the system optionally oversamples the incoming signals by a factor of approximately $n_{OS}$, where $n_{OS}$ is a selected positive number, such as $n_{OS}$=2–5, with $n_{OS}$=3 preferred. In step 83, the system filters the incoming signals, for example, using a low pass filter, such as a fourth order Bessel anti-aliasing filter with a cut-off frequency of 1–2 kHz. In step 85, the system downsamples by a factor of $n_{ds} \approx 1/n_O$. For example, if $n_{OS}$=3 is chosen, the incoming data may be initially sampled at 6000 samples/sec, then filtered, then downsampled to 6000/$n_{OS}$=2000 samples/sec, thus permitting use of frequencies up to about 1 kHz without aliasing, according to the Nyquist criterion.

In step 87 (optional), the filtered signals sf(t;d;m) are compared for each instance of a single gesture, a single test subject and a single sensor channel, and filtered signals corresponding to misformed gestures are deleted.

Each surviving filtered signal sf(t;d;m) is analyzed and segmented into approximately "equal-energy" or "equal variance" time segments, in step 89 (optional). This segmentation process examines the magnitude $|sf(t'_i;d;m)|$ and/or the gradient $|\Delta sf(t'_i;d;m)|$ of the filtered signal at a chosen subset (optionally, the entire set) $\{t'_i\}$ (i=1, ..., N') of time-sampling points and determines a segmentation subset $\{t''_j\}$ (j=1, ..., N"≦N') for which a sequence of selected interval functions $$IF(t''_j,t''_j+1)=IF\{sf(t;d;m), \Delta sf(t;d;m)|t''_j \leq t \leq t''_j+1\} \quad (1)$$

have approximately equal values. For example, the interval function may be defined as $$IF(t''_j,t''_j+1)=a_j \cdot \int \{|sf(t;d;m)|^p \, dt\}^{1/p}+b_j \cdot \int \{|\Delta sf(t;d;m)|^q \, dt\}^{1/q}, \quad (2)$$

where $a_j$ and $b_j$ are selected non-negative numbers and p and q are selected positive numbers. The time values $t''_j$ and $t''_{j+1}$ are chosen so that the numbers $IF(t''_j,t''_{j+1})$ are approximately equal to each other in the segmentation process.

In step 91 (optional), the individual filtered and surviving signals for the single gesture, the single test subject and the single sensor channel are concatenated into a single training file signal, designated ST(t;m) for each sensor channel m=1, ..., M (M≧2), with the associated segmentations of the time values. For our initial aircraft joystick gesture experiments and our initial bioelectric potential gesture experiments, the number of channels used were M=4 and M=8, respectively.

In step 93, a sequence of overlapping time averages OTA of magnitudes of the signals sf(t;d;m) over selected time segments, $tpi \leq t \leq tpi'$, are formed (referred to herein as overlapping time averages), defined as $$OTA(i;d;m) = \int |sf(t;d;m)| dt / (tpi' - tpi). \quad (3)$$

$$tpi \leq t \leq tpi'$$

where "i" identifies a time coefficient index, "d" identifies the particular test of the (single) gesture and m identifies the channel monitored. A particular group of time coefficients (i) will have substantially larger time averages OTA(i;d;m) for any fixed choice of d and m, and the signal sf(t;d;m) is said to be "centered" in those segments. For example, if overlapping time averages OTA(i;d;m) are formed with 128 consecutive samples at a net sampling rate of 2000 samples/sec, the time values tpi and tpi' would be chosen so that $$tpi' - tpi = (128)/2000 = 0.064 \text{ sec}, \quad (4)$$

and the next time segment would overlap this segment by a selected fraction f, such as 75 percent (96-sample overlap) or 87.5 percent (112-sample overlap). Any reasonable sampling interval, $tpi \leq t \leq tpi'$, may be used here. However, the sampling interval length, tpi'−tpi, need not be uniform for all time coefficients (i). The overlap fraction f, indicated by the relation $$tp(i+1) - tpi = (1-f)(tpi' - tpi), \quad (5)$$

can also be variable and ranges from 0.5 to 0.9, or higher if necessary.

The sampling interval, $tpi \leq t \leq tpi'$, has a time coefficient or index i. FIG. 6B indicates that the sequence of time coefficients i is decomposed into Q consecutive, preferably non-overlapping intervals Q or "states", where Q is a selected number that may range from 2 to 20, or even higher if desired. In the example shown in FIG. 6B, Q=8. Once the number Q of states is chosen, the time coefficients i corresponding to each state index q (q=1, 2, . . . , Q) are determined as follows. In step 95, the variance $\sigma((i;m)^2$ is calculated for each time coefficient i and each channel (m). The individual variances $\sigma((i;m)^2$ are defined by sums over the N tests or instantiations (d) as $$\sigma(i;m)^2 = \sum_{d=1}^{N} \{OTA(i;d;m) - \mu(i;m)\}^2 / N \quad (6)$$

$$\mu(i;m) = \sum_{d=1}^{N} OTA(i;d;m)/N. \quad (7)$$

A variance area $\sigma_A^2$ is now calculated by $$\sigma_A^2 = \sum_i \sum_m \sigma(i;m)^2, \quad (8)$$

with an average value per state of $\sigma_A^2/Q$.

In step 97, the individual variance contributions, $\sigma(i;m)^2$, are divided into Q groups or clusters of approximately equal size, in the following manner. Calculate a time slice contribution, $\sigma(i)^2$, as a partial sum $$\sigma(i)^2 = \sum_m \sigma(i;m)^2, \quad (9)$$

with i=1, 2, . . . , and determine the lowest positive integers I1, I2, I3, etc. for which $$\sum_{i=1}^{I1-1} \sigma(i)^2 < \sigma_A^2/Q \leq \sum_{i=1}^{I1} \sigma(i)^2, \quad (10)$$

$$\sum_{i=Iq+1}^{I(q+1)-1} \sigma(i)^2 < \sigma_A^2/Q \leq \sum_{i=Iq+1}^{I(q+1)} \sigma(i)^2, (q = 1, 2, \ldots, Q-1)., \quad (11)$$

where I0=0 for consistency. Each of the i-index intervals, $I(q-1)+1 \leq i \leq Iq$ (q=1, 2. . . . , Q), contains a sufficient number of time slice contributions $\sigma(i)^2$ to make an approximately equal contribution to the variance area $\sigma_A^2$, namely $\sigma_A^2/Q$. For ease of reference, the state time interval is defined as $$\tau(q-1;q) = \{t | tpi \leq t \leq tpi'; I(q-1)+1 \leq i \leq Iq\}. \quad (12)$$

K-means clustering creates a plurality of means and variances, one of an each corresponding to each of two or more Gaussian distributions that are Al part of a mixture of Gaussian distributions within a given state. Calculation of K-means clusters for a multivariate probability distribution is discussed by J. MacQueen in "Some models for classification and analysis of multivariate distributions", published in the *Fifth Berkelev Symposium on Mathematical Statistics and Probability*, vol. 1, University of California Press, Berkeley and Los Angeles, 1967, pp. 281–297. The information contained in this article is incorporated herein. The K-means mean values $\mu$(m) may be calculated separately for each sensor channel (m), using Eq. (7), for example.

The quantity OTA(i;d;m) defined in Eq. (3) can be generalized, for example, by (re)defining the symbol OTA to be $$OTA(i;d;m) = \{\{u_i \int |sf(t;d;m)|^r dt\}^{1/r} + \{u'_i \int |sf(t;d;m)|^{r'} dt\}^{1/r'} + \{u''_i \int |\Delta 2 sf(t;d;m)|^{r''} dt\}^{1/r''}\}/(tpi' - tpi), \quad (13)$$

$$\Delta 1 sf(t;d;m) = sf(t + \Delta t1;d;m) - sf(t - \Delta t2;d;m), \quad (14A)$$

$$\Delta 2 sf(t;d;m) = sf(t + \Delta t3;d;m) - 2sf(t;d;m) + sf(t + \Delta t4;d;m), \quad (14B)$$

where: $u_i$, $u'_i$, and $u''_i$, are selected non-negative weight coefficients that may depend upon the time coefficient i; r, r' and r" are selected positive numbers; and $\Delta t1$, $\Delta t2$, $\Delta t3$ and $\Delta t4$ are selected time increments. Other generalizations of the OTA values defined in Eq. (3) may also be used here.

A hidden Markov model (HMM) analysis is now performed on the time coefficients i for the OTA signals. One suitable variable here is an M-dimensional column feature vector, defined in step 101 as $$fv(i;q(i)) = \{OTA(i;m=1), OTA(i;m=2), \ldots, OTA(i;m=M)\}^{tr} (t \epsilon \tau(q(i)-1;q(i))). \quad (15)$$

In step 103, two consecutive M-dimensional states, q(i) and q(i+1), of the system are related by an M×M transition matrix $T(q(i)) \rightarrow q(i+1))$ by a relation $$q(i+1) = T(q(i) \rightarrow q(i+1))q(i) \ (q(i)=1, 2, \ldots, Q) \quad (16)$$

where the transition matrices $T(q(i) \rightarrow q(i+1))$ are not yet known and will depend upon the time interval (i). The state index q(i) changes, where the time coefficient i is replaced by i+1, only for i=I1, I2, . . . , IQ. For all other values of i, the transition q(i)→q(i+1) produces no change of state q. An assembly of state vectors sv(q(i)) and corresponding set of time coefficient transition values, designated as {sv(q(Ik);q (Ik)} (k=0, 1, ..., Q), defines the set of states the system passes through for a selected gesture.

The transition matrix T(q(i)→q(i+1)) is initialized and is arranged to follow left-to-right, non-ergodic matrix transitions so that the system does not return to any M-dimensional state after the system has passed through and beyond that state in a transition sequence. In a sequence of left-to-right non-ergodic transitions over set of discrete states, as described by Rabiner and Juang, ibid, the corresponding transition matrices are upper triangular, having only zero value transition probabilities below the diagonal for the transition matrices T(q(i)→q(i+1)). Where only left-to-right, non-ergodic transitions are present, estimation of the entries of the transition probability matrices T(q(i)→q (i+1)) is simpler, as discussed by Rabiner and Juang, ibid. Initially, the transition matrix T(q(i)→q(i+1)) for i=1 is strongly diagonal with diagonal entries ≈0.9. This concludes the training portion of analysis of bioelectric potentials that are produced by a selected gesture.

For each of a selected group of gestures, the (hidden) states q=1, ..., Q are estimated or identified, using the transition relation (16). Each gesture may have the same number or a different number Q of states and different transition matrices T(q(i)→q(i+1)) and, one hopes, an ordered set of states that can be distinguished from an ordered set of states corresponding to a different gesture.

Assume that a selected volitional gesture (not identified as yet) is performed, thus producing a sequence of bioelectric potentials (BPs) that are monitored and recorded on each of M channels. These potentials are processed as described in the preceding, and HMM analysis is applied to the sampled BP sequence, for each channel (m) and for each time coefficient (i), to produce estimated state and state transition pairs {sv'(q'(Ik'));q'(Ik')} (k'=0, 1, ..., Q') that are compared with the ordered sequences of states and state transition pairs for each of a selected set of already-tested reference gestures. Using numerical values provided by one or more selected similarity metrics or other criteria $$\Phi\{\{sv(q(Ik));q(Ik)\}, \{sv'(q'(Ik'));q'(Ik')\}\},$$

the observed or calculated assembly {sv'(q'(Ik'), q'(Ik')} for the volitional gesture is compared with the reference assemblies {sv(q(Ik);q(Ik) } for each of the reference gestures. If the metric Φ{{sv(q(Ik);q(Ik)}, {sv'(q'(Ik');q'(Ik')}} is above a selected threshold value (or below a selected threshold value) for a particular reference gesture, the observed gesture is interpreted as being "close to" the reference gesture. Alternatively, a metric value Φ{{sv(q(Ik);q(Ik)}, {sv'(q' (Ik'); q'(Ik')}} is calculated for each reference gesture, and the reference value that produces the highest metric value (or the lowest metric value) Φ{{sv(q(Ik);q(Ik)}, {sv'(q'(Ik') ;q'(Ik')}} is interpreted to be the reference gesture that is "closest" to the observed gesture. As a second condition, this "closest" reference gesture may not be accepted as a legitimate representative of the given gesture unless the metric value Φ{{sv(q(Ik);q(Ik)}, {sv'(q'(Ik');q'(Ik')}} for this reference gesture is above (or below) a selected threshold value. This analysis is applied to each of the state vectors, represented by the sequence of vectors sv(q(Ik)}. One method of such analysis is the Viterbi analysis of optimum node-to-node paths in a network, as described by A. Viterbi, ibid, and by B. Sklar, ibid.

Figure 9A:
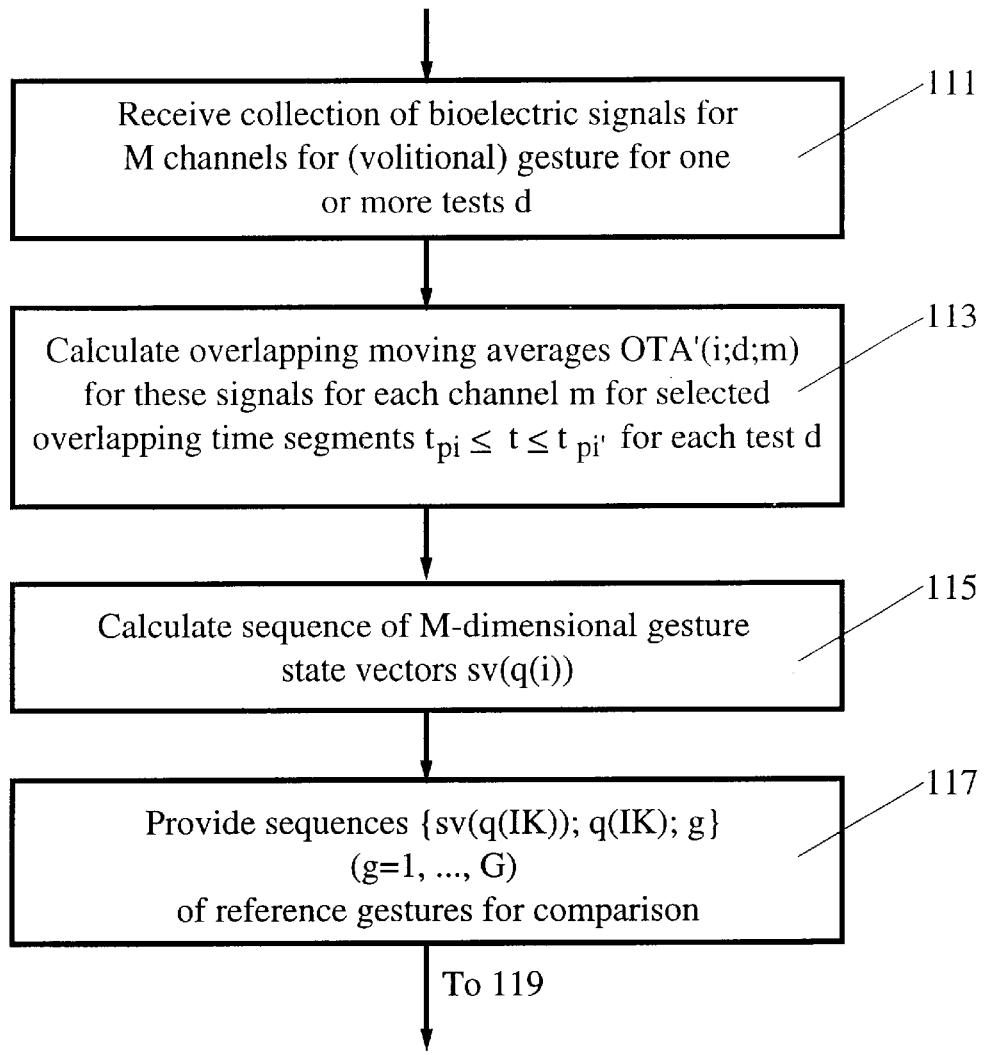
Figure 9B:
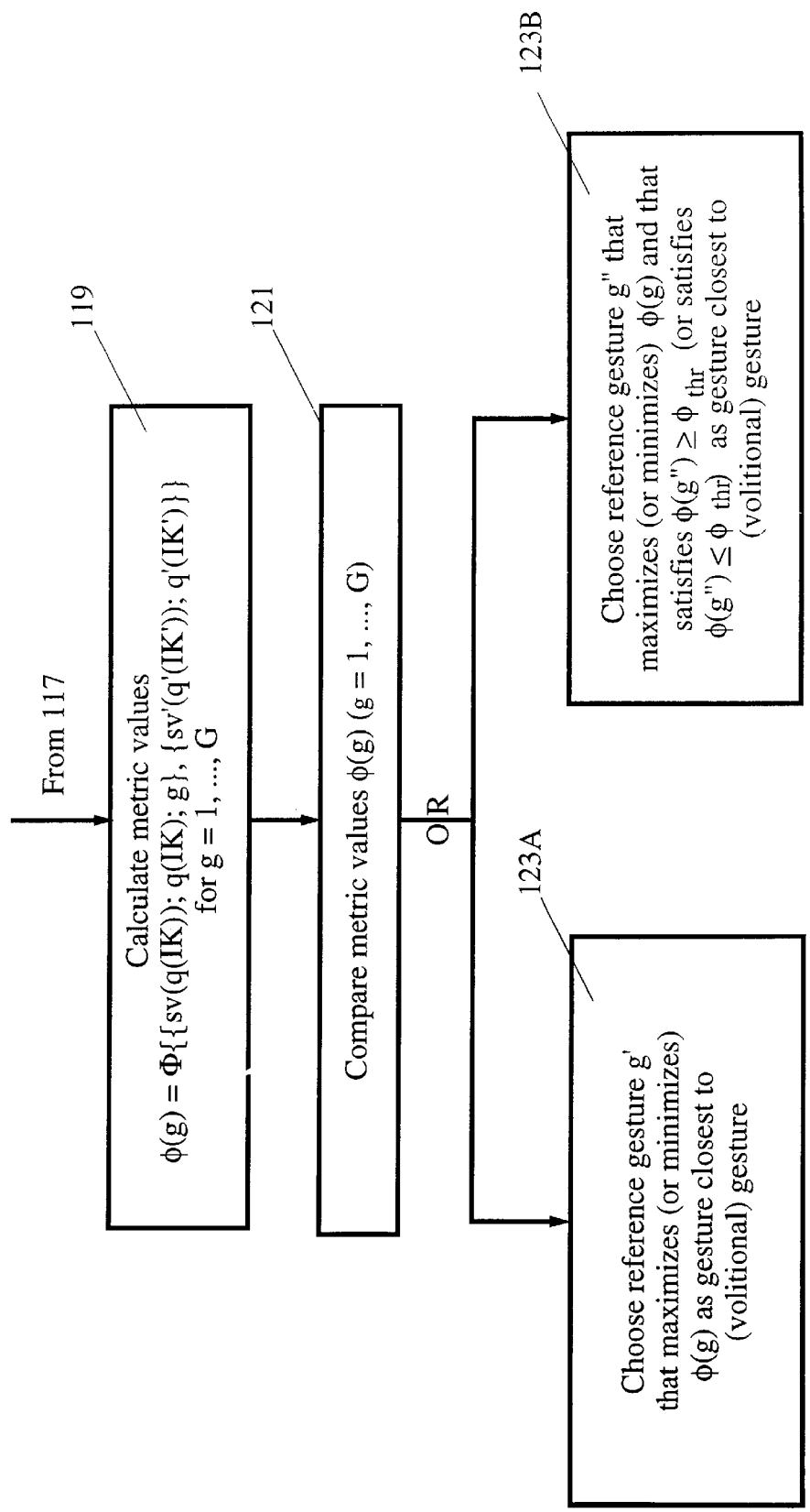

This "recall" procedure is illustrated in a flow chart in FIG. 9. In a first step 111, a collection of time-ordered bioelectric potential signals is received for M channels, corresponding to a volitional gesture that is likely j unknown as yet. In step 113, overlapping moving averages OTA' (i;d;m) of in these signals are formed for each channel for each of a sequence of selected, overlapping time segments, tpi≦t≦tpi', as discussed in the preceding development. Where the collection of signals refer to only one test of a gesture, the test variable d is ignored. Where the collection of signals refer to two or more tests of a gesture, the test variable d may be retained and used to index each of these tests. In step 115, a sequence of M-dimensional feature vectors sv'(i;q'(i)) is calculated for the volitional gesture, as in Eq. (13), using a Viterbi analysis, as discussed in the Viterbi article, ibid.

In step 117, sequences of two or more reference gesture state vectors {sv(q(Ik));q(Ik);g}, numbered g=1, 2, ..., G (G≧2), are provided for comparison. In step 119, the sequence of gesture state vectors {sv'(q'(Ik'));q'(Ik')} for the volitional gesture is compared with each of the G known reference sequences {sv(q(Ik));q(Ik);g}, using the selected metric Φ to calculate a value $$\phi(g)=\Phi\{\{sv'(q'(Ik'));q'(Ik')\}, \{sv(q(Ik));q(Ik);g\}\}. \quad (17)$$

In step 121, the values φ(g) (g=1, ..., G) are compared with each other for each reference gesture to obtain an extremum value (maximum or minimum) for φ(g). Optionally, the extremum value for φ(g)_ is compared with a threshold metric value $\phi_{thr}$.

In step 123A, if a reference gesture corresponding to a gesture numbered g' satisfies $$\phi(g')=\max_g \phi(g) \ (g=1, \ldots, G), \quad (18)$$

the volitional gesture is interpreted to be, or to be closest to, the gesture numbered g'.

Alternatively, in step 123B, if a reference gesture corresponding to a gesture numbered g" satisfies $$\phi(g'')=\max_g \phi(g) \ (g=1. \ldots, G), \quad (19)$$

and satisfies $$\phi(g'')\geq\phi_{thr}, \quad (20)$$

the volitional gesture is interpreted to be, or to be closest to, the gesture numbered g". The maximum function in Eq. (19) and the inequality "≧" in Eq. (20) can be replaced by a minimum function and the inequality "≦", respectively, depending upon the choice of metric Φ used for the comparison.

The metric Φ can be constructed in many ways. For example, a difference of the M-dimensional feature vectors fv(i;q(i)) for the volitional gesture and for each of the reference gestures (g=1, ..., G) can be formed, and the metric value φ(g) can be defined as $$\phi(g) = \left\{\sum_{k=1}^{K} w_k \cdot \|fv'(Ik; q'(Ik)) - fv(Ik; q(Ik); g)\|^r \right\}^{1/r}, \quad (21)$$

where ∥x∥ is a non-negative, real valued norm for an M-dimensional vector x, r is a selected positive number and $w_k$ is a selected non-negative weighting coefficient. For example, the norm of a vector x with components {$x_1$, ..., $x_M$} may be defind as $$\|x\| = \sum_{m=1}^{M} c_m \cdot |x_m|, \qquad (22)$$

where $c_m$ is a selected non-negative weighting coefficient.

The metric $\Phi$ can also be constructed using the difference of corresponding state vectors $sv(q(Ik))$ for the volitional gesture and for each of the reference state vectors:

$$\phi(g) = \left\{ \sum_{k=1}^{K} w'_k \cdot \|sv'(q'(Ik)) - sv(q(Ik); g)\|^{r'} \right\}^{1/r'}, \qquad (23)$$

where $\|x\|$ is a non-negative, real valued norm for an M-dimensional vector x, r' is a selected positive number and $w'_k$ is a selected non-negative weighting coefficient.

The metric $\Phi$ can also be constructed using the construction of probability of observing an ordered sequence of state representatives, O1, O2, . . . , Qi and the state-to-state transition probabilities $T(q(i){\rightarrow}q(i{+}1))$ and the construction of the associated forward (probability) variables $\alpha(i)$, as discussed in the Rabiner HMM review article, pp. 262–263. In this construction, the forward variables $\alpha((i;g)$ for a reference gesture, numbered g, are compared with the corresponding forward variables $\alpha'(i)$ for the volitional gesture, using a norm or metric value such as $$\phi(g) = \left\{ \sum_{k=1}^{K} w''_i \cdot \|\alpha'(i) - \alpha(i; g)\|^{r''} \right\}^{1/r''}, \qquad (24)$$

where $w''_k$ is a selected non-negative weight coefficient, r" is a selected positive number and $\|x\|$ denotes a norm, in a space of suitable dimension, of the variable or vector x. Using the metric $\Phi$, however defined, one goal is to choose the index g so that $\phi(g)$ is as small as possible (or as large as possible), and is optionally no greater than (no less than) a selected threshold value $\phi_{thr}$. Other metrics $\Phi$ can also be constructed to compare each of the reference gestures with the volitional gesture.

What is claimed is:

1. A method for providing an interface for control of an instrument, the method comprising:

receiving electrical signals at at least two selected, spaced apart locations on a person's body that are generated in association with a selected gesture executed by the person, over a selected time interval;

electronically processing the at least two electrical signals to identify at least one signal characteristic that is associated with the selected gesture by a process comprising:

forming a sequence of at least two windows, each having a selected number w1 of samples of the received signals, where the at least two windows overlap each other by a selected number w2 of samples;.

forming an average of magnitudes of values of the received signals within each of the at least two windows;

determining a sequence of at least two state vectors that represent an average of magnitudes of values of the received signals within at least two selected time segments that are determined with reference to the at least two windows; and performing a hidden Markov modeling process on the at least two state vectors that are associated with the selected gesture.

2. The method of claim 1, further comprising responding to receipt of a signal having said at least one signal characteristic as if said selected gesture had been performed on said instrument, without requiring that said gesture be represented in a visually perceptible manner.

3. The method of claim 1, wherein said selected gesture is drawn from a group of relatively coarse gestures consisting of: a stop motion; making a fist; making a come motion; making a thumb up motion; making a thumb down motion; moving an arm from a first position to a second position; and moving said person's head in a selected direction.

4. The method of claim 1, wherein said selected gesture is drawn from a group of relatively fine gestures consisting of:

tapping at least one finger; reaching for and depressing at least one key on a keyboard;

moving a joystick in at least one of the directions forward, backward, right and left;

touching a joystick without movement of the joystick; and grasping and moving a stylus to a selected location.

5. The method of claim 1, wherein said selected gesture is chosen to be grasping a writing instrument and forming at least one character using cursive writing.

6. The method of claim 1, further comprising displaying at least one result of said electronically processed signals in at least one of a graphical format and an alphanumeric format.

7. A system for providing an interface for control of an instrument, the system comprising a computer that is programmed:

to receive electrical signals at at least two selected, spaced apart locations on the person's body that are generated in association with a selected gesture by a person, over a selected time interval; and to electronically process the at least two electrical signals to identify at least one signal characteristic that is associated with the selected gesture by a process comprising:

forming a sequence of at least two windows, each having a selected number w1 of samples of the received signals, where the at least two windows overlap each other by a selected number w2 of samples;

forming an average of magnitudes of values of the received signals within each of the at least two windows;

determining a sequence of at least two state vectors that represent an average of magnitudes of values of the received signals within selected time segments that are determined with reference to the at least two windows; and performing a hidden Markov modeling process on the at least two state vectors that are associated with the selected gesture.

8. The system of claim 7, wherein said computer is further programmed to respond to receipt of a signal having said at least one signal characteristic as if said selected gesture had been performed on said instrument, without requiring that said gesture be represented in a visually perceptible manner.

9. The system of claim 7, wherein said computer is further programmed to draw said at least one selected gesture from a group of relatively coarse gestures consisting of: a stop motion; making a fist; making a come motion; making a thumb up motion; making a thumb down motion; moving an arm from a first position to a second position; and moving said person's head in a selected direction.

10. The system of claim 7, wherein said computer is further programmed to draw said selected gesture from a group of relatively fine gestures consisting of:

tapping at least one finger; reaching for and depressing at least one key on a keyboard;

moving a joystick in at least one of the directions forward, backward, right and left;

touching a joystick without movement of the joystick; and grasping and moving a stylus to a selected location.

11. The system of claim 7, wherein said computer is further programmed to analyze a gesture that comprises grasping a writing instrument and forming at least one character using cursive writing.

12. The system of claim 7, wherein said computer is further programmed to display at least one result of said electronically processed signals in at least one of a graphical format and an alphanumeric format.

13. A method for identifying a gesture received at an interface for control of an instrument, the method comprising:

receiving electrical signals at at least M selected, spaced apart locations ($M \geq 2$) on a person's body that are generated in association with a volitional gesture executed by the person, over a selected time interval;

providing a sequence of averages of magnitudes of the received signals, designated OTA'(i;m), determined with reference to selected time partition intervals, $tpi \leq t \leq tpi'$, for each of a set of states, numbered $q'=1, 2, \ldots, Q'$ where $Q'$ is a selected integer $\geq 2$, and providing an M-dimensional vector $$fv'(i;q'(i)) = \{OTA'(i;m=1), \ldots, OTA'(i;m=M)\}^{tr}$$

as a representative of a state in the time partition interval $tpi \leq t \leq tpi'$;

providing a transition matrix, designated $T'(q'(i) \rightarrow q'(i+1))$ that connects the state number $q'(i)$ and the state number $q'(i+1)$ $(=1, \ldots, Q'-1)$ by a relation $$q'(i+1) = T(q(i) \rightarrow q(i+1))q'(i),$$

for at least one of the pairs of states $(q-1,q)$;

identifying the collection of vectors $\{fv'(i;q'(i))\}$ $(i=1, 2, \ldots)$ with the volitional gesture;

performing a hidden Markov modeling process on the collection of vectors $\{fv'(i;q'(i)\}$ to determine a collection of state vectors $\{sv'(q(Ik))\}$, for selected values $i=Ik$, corresponding to the volitional gesture;

providing G sets of M-dimensional reference state vectors $sv(q(Ik);g)$, numbered $g=1, \ldots, G$ with $G \geq 2$, with each set of reference state vectors numbered g corresponding to a reference gesture;

for each reference state vector $sv(q(Ik);g)$, calculating a metric value $f(g)$ defined by $$f(g) = F\{\{sv'(q'(Ik));q'(Ik)\};\{sv(q(Ik);g);qk)\}\},$$

where F is a selected metric function;

comparing the values $f(g)$ for $g=1, \ldots, G$, and identifying an index $g=g'$ for which $f(g')$ is an extremum value drawn from the group of extremum values consisting of $f(g')=\max_g f(g)$ and $f(g')=\min_g f(g)$; and interpreting the reference gesture corresponding to the index $g=g'$ as the gesture that is closest to the volitional gesture.

14. The method of claim 13, further comprising: interpreting said reference gesture corresponding to said index $g=g'$ as substantially identical to said volitional gesture only if said metric value $f(g')$ is at least equal to a selected threshold value $f_{thr}$.

15. The method of claim 13, further comprising choosing said metric value $f(g)$ by a process comprising:

providing G sets of collections of M-dimensional reference vectors $\{fv(i;q(i);g)\}$, numbered $g=1, \ldots, G$, associated with said reference gestures and corresponding to said collection of vectors $\{fv'(i;q(i))\}$; and identifying said metric value $f(g)$ with the value $$\left\{ \sum_{k=1}^{K} w_k \cdot \|fv'(Ik; q'(Ik)) - fv(Ik; q(Ik); g)\|^r \right\}^{1/r},$$

where $\|x\|$ designates a non-negative, real valued norm associated with an M-dimensional vector x, $\{Ik\}$ $(k=1, \ldots, K; K \geq 2)$ is a selected set of values of said index i, r is a selected positive number and $w_k$ is a selected non-negative weighting coefficient.

16. The method of claim 13, further comprising choosing said metric value $f(g)$ by a process comprising:

identifying said metric value $f(g)$ with the value $$\left\{ \sum_{k=1}^{K} w'_k \cdot \|sv'(q'(Ik)) - sv(q(Ik); g)\|^{r'} \right\}^{1/r'},$$

where $\|x\|$ designates a non-negative, real valued norm associated with an M-dimensional vector x, $\{k\}$ $(k=1, \ldots, K; K \geq 2)$ is a selected set of values of said index i, r' is a selected positive number and $w'_k$ is a selected non-negative weighting coefficient.

17. The method of claim 13, further comprising causing said instrument to respond to receipt of said electrical signals corresponding to said volitional gesture as if said reference gesture corresponding to said index $g=g'$ had been performed on said instrument.

18. A system for providing an interface for control of an instrument, the system comprising a computer that is programmed:

to receive electrical signals at at least M selected, spaced apart locations ($M \geq 2$) on a person's body that are generated in association with a volitional gesture executed by the person, over a selected time interval;

to provide a sequence of averages of magnitudes of the received signals, designated OTA'(i;m), determined with reference to selected time partition intervals, $tpi \leq t \leq tpi'$, for each of a set of states, numbered $q'=1, 2, \ldots, Q'$ where $Q'$ is a selected integer $\geq 2$, and to provide an M-dimensional vector $$fv'(i;q'(i)) = \{OTA'(i;m=1), \ldots, OTA'(i;m=M)\}^{tr}$$

as a representative of a state in the time partition interval $tpi \leq t \leq tpi'$;

to provide a transition matrix, designated $T'(q'(i) \rightarrow q'(i+1))$ that connects the state number $q'(i)$ and the state number $q'(i+1)$ $(=1, \ldots, Q'-1)$ by a relation $$q'(i+1) = T(q(i) \rightarrow q(i+1))q'(i),$$

for at least one of the pairs of states $(q-1,q)$;

to identify the collection of vectors $\{fv'(i;q'(i))\}$ $(i=1, 2, \ldots)$ with the volitional gesture;

to perform a hidden Markov modeling process on the collection of vectors $\{fv'(i;q'(i)\}$ to determine a collection of state vectors {sv'(q(Ik))}, for selected values i=Ik, corresponding to the volitional gesture;

to provide G sets of M-dimensional reference state vectors sv(q(Ik);g), numbered g=1, . . . , G with G≧2, with each set of reference state vectors numbered g corresponding to a reference gesture;

for each reference state vector sv(q(Ik);g), to calculate a metric value f(g) defined by $$f(g)=F\{\{sv'(q'(Ik));q'(Ik)\};\{sv(q(Ik);g);q(Ik)\}\},$$

where F is a selected metric function;

for each reference vector fv(i;q(i);g), to calculate a metric value f(g) defined by $$f(g)=F\{fv(i;q'(i));fv(i;q(i);g)\},$$

where F is a selected metric function;

to compare the values f(g) for g=1, . . . G, and to identify an index g=g' for which f(g') is an extremum value drawn from the group of extremum values consisting of f(g')=max$_g$f(g) and f(g')=min$_g$f(g); and to interpret the reference gesture corresponding to the index g=g' as the gesture that is closest to the volitional gesture.

19. The system of claim 18, wherein said reference gesture corresponding to said index g=g' is interpreted as substantially identical to said volitional gesture only if said metric value f(g') is at least equal to a selected threshold value $f_{thr}$.

20. The system of claim 18, wherein said computer is further programmed to choose said metric value f(g) by a process comprising:

providing G sets of collections of M-dimensional reference vectors {fv(i;q(i);g)}, numbered g=1, . . . , G, associated with said reference gestures and corresponding to said collection of vectors {fv'(i;q(i))}; and identifying said metric value f(g) with the value $$\left\{\sum_{k=1}^{K} w_k \cdot \|fv'(Ik; q'(Ik)) - fv(Ik; q(Ik); g)\|^r\right\}^{1/r},$$

where ∥x∥ designates a non-negative, real valued norm associated with an M-dimensional vector x, {Ik} (k=1, . . . , K; K≧2) is a selected set of values of said index i, r is a selected positive number and $w_k$ is a selected non-negative weighting coefficient.

21. The system of claim 18, wherein said computer is further programmed to choose said metric value f(g) by a process comprising:

identifying said metric value f(g) with the value $$\left\{\sum_{k=1}^{K} w'_k \cdot \|sv'(q'(Ik)) - sv(q(Ik); g)\|^{r'}\right\}^{1/r'},$$

where ∥x∥ designates a non-negative, real valued norm associated with an M-dimensional vector x, {Ik} (k=1, . . . , K; K≧2) is a selected set of values of said index i, r' is a selected positive number and w'$_k$ is a selected non-negative weighting coefficient.

22. The system of claim 18, wherein said computer causes said instrument to respond to receipt of said electrical signals corresponding to said volitional gesture as if said reference gesture corresponding to said index g=g' had been performed on said instrument.

\* \* \* \* \*